US005294545A

United States Patent [19]
Son et al.

[11] Patent Number: 5,294,545
[45] Date of Patent: Mar. 15, 1994

[54] CONCATEMERIC DNA LENGTH STANDARDS

[75] Inventors: Marjatta Son; Philip Serwer, both of San Antonio, Tex.

[73] Assignee: Board of Regents, The University of Texas, Austin, Tex.

[21] Appl. No.: 725,048

[22] Filed: Jul. 3, 1991

Related U.S. Application Data

[63] Continuation of Ser. No. 293,235, Jan. 4, 1989, Pat. No. 5,030,566.

[51] Int. Cl.$^5$ .................... C12P 19/34; G01N 27/26
[52] U.S. Cl. .................... 435/91.53; 435/6; 435/172.3; 435/320.1; 204/182.8; 536/23.1
[58] Field of Search .............. 435/172.3, 6, 91, 320.1; 536/27, 2.1, 23.71; 204/182.2

[56] References Cited

U.S. PATENT DOCUMENTS

| | | | |
|---|---|---|---|
| 4,473,452 | 9/1984 | Cantor et al. | 204/182.8 |
| 4,650,761 | 3/1987 | Hershberger et al. | 436/91 |
| 4,710,465 | 12/1987 | Weissman et al. | 435/91 |
| 4,784,952 | 11/1988 | Ludwig et al. | 435/91 |
| 5,030,566 | 7/1991 | Son et al. | 435/91 |
| 5,041,203 | 8/1991 | Serwer | 204/299 |

OTHER PUBLICATIONS

White, Dissertation, "Formation and Processing of Concatemers of Bacteriophage T7 DNA, In Vitro", Harvard Medical School, Harvard University, (1987).
Fröhlich et al., *Virology*, vol. 65, 1975, pp. 455–468.
Son et al., *Virology*, vol. 162, 1988, pp. 38–46.
Waterbury et al., *Nuc. Acids Res.*, vol. 15, 1987, p. 3930.
Serwer et al., *Electrophorosis*, vol. 8, 1987, pp. 224–246.
Ritchie et al., "Terminal Repetition in Non-permuted T3 and T7 Bacteriophage DNA Molecules," J. Mol. Biol. 23:365–376 (1967).
Kelly, T. J. and Thomas, C. A. "An Intermediate in the Replication of Bacteriophage T7 DNA Molecules," J. Mol. Biol. 44:459–475 (1969).
Kerr, C. and Sadowski, P. D. "Packaging and Maturation of DNA of Bacteriophage T7 In Vitro," Proc. Nat. Acad. Sci. USA 71:3545–3549 (Sep. 1974).
Sadowski et al., "Terminal Cross-linking of DNA Catalyzed by an Enzyme System Containing DNA Ligase, DNA Polymerase, and Exonuclease of Bacteriophage T7," Can. J. Biochem. 52:525–535 (1974).
Miller et al., "The Role of Bacteriophage T7 Exonuclease (Gene 6) in Genetic Recombination and Production of Concatemers," J. Mol. Biol. 101:223–234 (1976).
Fangman, W., "Separation of Very large DNA molecules by gel electrophoresis," Nuc. Acids Res. 5:653–665 (1978).
Kuemmerle, N. B. and Masker, W. E., "In Vitro Packaging of UV Radiation Damaged DNA from Bacteriophage T7," J. Virol. 23:509–516 (1977).
Sadowski, P. D., "Genetic Recombination of Bacteriophage T7 DNA In Vitro, II. Further Properties of the In Vitro Recombination-Packaging Reaction," Virol. 78:192–202 (1977).
Langman et al., "The structure and maturation of intermediates in bacteriophage T7 DNA replication", Can. J. Biochem 56:508–516 (1978).
Masker et al., "In Vitro Packaging of Bacteriophage T7 DNA Synthesized In Vitro", J. Virol. 27:149–163 (1978).

(List continued on next page.)

*Primary Examiner*—Richard A. Schwartz
*Assistant Examiner*—James Ketter
*Attorney, Agent, or Firm*—Arnold, White & Durkee

[57] ABSTRACT

The use of T7 bacteriophage to produce DNA length standards by enzymatically joining terminally repetitious, blunt-ended DNA has now been demonstrated. It is now possible to precisely control the formation of concatemeric DNAs thereby generating custom-made size-ranges of length standards. Furthermore, the standards thus produced are stable over time providing a highly reproducible and convenient product for the molecular biologist.

20 Claims, 3 Drawing Sheets

OTHER PUBLICATIONS

Rosenberg et al., "Survey and Mapping of Restriction Endonuclease Cleavage Sites in Bacteriophage T7 DNA", J. Mol. Viol. 135:907–915 (1979).

Fujisawa et al., "In Vitro Formation of the Concatemeric DNA of Bacteriophage T3 and Its Biological Activity in the in Vitro Packaging Reaction", Virol. 101:327–334 (1980).

Fujisawa et al., "Purification of DNA-Binding Proteins of Bacteriophage T3 DNA and Their Role in In Vitro Packaging of Phage T3 DNA," Virol. 105:480–489 (1980).

Yamagishi et al., "Purification of Gene 6 Product of Bacteriophage T3 and Its Role in in vitro DNA Packaging", Virol. 100:382–389 (1980).

Serwer, P., "Electrophoresis of Duplex Deoxyribonucleic Acid in Multiple-Concentration Agarose Gels: Fractionation of Molecules with Molecular Weights between $2 \times 10^6$ and $110 \times 10^6$", Biochem. 19:3001–3004 (1980).

Serwer, P. and Greenhaw, G. A., "Fractionation of Concatemeric DNA of Bacteriophage T7 by Agarose Gel Electrophoresis", Electrophoresis (1981).

Serwer, P. and Watson, R. H., "Capsid-DNA Complexes in the DNA Packaging Pathway of Bacteriophage T7: Characterization of the Capsids Bound to Monomeric and Concatemeric DNA", Virol. 198:164–176 (1981).

Dunn, J. J. and Studier, F. W., "Complete Nucleotide Sequence of Bacteriophage T7 DNA and the Locations of T7 Genetic Elements", J. Mol. Biol. 166:477–535 (1983).

Furth, M. E. and Wickner, S. H., "Lambda DNA Replication", Lambda II, pp. 145–173 (1983).

Serwer et al., "Stability and In Vitro DNA Packaging of Bacteriophages: Effects of Dextrans, Sugars, and Polyols", J. Virol. 45:665–671 (Feb. 1983).

Studier, F. W. and Dunn, J. J., "Organization and Expression of Bacteriophage T7 DNA", Cold Spring Harbor Symposia on Quantitative Biology, vol. XLVII, pp. 999–1007 (1983).

Casjens, S., "Nucleic Acid Packaging by Viruses", Virus Structure and Assembly, pp. 76–147 (1985).

Lee, D. D. and Sadowski, P. D., "In vitro concatemerization of bacteriophage T7 DNA: Role in DNA synthesis and gene 6 exonuclease", Can. J. Biochem. Cell Biol. 63:237–242 (1985).

Anand, R., "Pulsed field gel electrophoresis: a technique for fractionating large DNA molecules", Trends Gen. 2:278–283 (1986).

Hamada et al., "A Defined in Vitro System for Packaging of Bacteriophage T3 DNA", Virol. 151:119–123 (1986).

Serwer, P. and Hayes, S. J., "A voltage gradient-induced arrest of circular DNA during agarose gel electrophoresis", Electrophoresis 8:244–246 (1987).

Serwer et al., "Multidimensional Analysis of Intracellular Bacteriophage T7 DNA: Effects of Amber Mutations in Genes 3 and 19", J. Virol. 61:3499–3509 (1987).

Serwer, P., "Gel electrophoresis with discontinuous rotation of the gel: An alternative to gel electrophoresis with changing direction of the electrical field", Electrophoresis 8:301–304 (1987).

Shibata et al., "Characterization of the Bacteriophage T3 DNA Packaging Reaction in Vitro in a Defined System", J. Mol. Biol. 196:845–851 (1987).

Son, M. and Serwer, P., "The Kinetics of Bacteriophage T7 DNA Packaging in Vitro", Abstract Proc. Am. Soc. Biol. Chemists (1987).

White, J. H. and Richardson, C. C., "Processing of Concatemers of Bacteriophage T7 DNA in Vitro", J. Biol. Chem. 262:8851–8860 (1987).

White, J. H. and Richardson, C. C., "Gene 18 Protein of Bacteriophage T7, Overproduction, Purification and Characterization," J. Biol. Chem. 262:8845–8850 (1987).

Son et al., "Concatemerization and Packaging of Bacteriophage T7 DNA in Vitro: Determination of the Concatemer's Length and Appearance Kinetics by Use of Rotating Gel Electrophoresis," Virol. 162:38–46 (1988).

Watson et al., "The Replication of Bacterial Viruses", Molecular Biology of the Gene, vol. 1, 4th Ed., pp. 298–299, 503–548 (1987).

DNASTAR, *The Lambda Ladder*, High Molecular Weight Marker, Product Announcement Memorandum (1988).

FMC BioProducts, Size Standards for Megabase DNA, Product Announcement Memorandum (1988).

Calendar, R. (Ed.), "The Bacteriophages", vol. 1, pp. 259–289, 439–475 (date of publ. unknown).

Serwer, P. and Hayes, S. J., "A New Mode of Rotating Gel Electrophoresis For Fractionating Linear and Circular Duplex DNA: The Effects of Electrophoresis During the Gel's Rotation", Appl. Theor. Electrophoresis.

CONCATEMERIC DNA LENGTH STANDARDS

The National Institutes of Health provided funding used in part for this invention under grant GM 24365. Accordingly, the Federal Government may have certain rights in this invention pursuant to 35 U.S.C. 202.

This application is a continuation of application Ser. No. 07/293,235, filed Jan. 4, 1989 now U.S. Pat. No. 5,030,566.

BACKGROUND OF THE INVENTION

A. Field of the Invention

The present invention describes a method for producing DNA length standards useful in sizing long DNA molecules (40–600+kb) typically encountered when working with chromosomal DNA, for example during chromosomal mapping, or with large viral and plasmid DNA. Specifically, the invention is a method for enzymatically constructing such standards by use of crude cell extracts and with the realization of both a previously unattainable stability of the standards and control of their length.

B. Description of the Related Art

As the study of molecular biology evolved, workers in this field strived to manipulate and fractionate by size larger and larger pieces of DNA using the molecular tools previously successful on smaller fragments of DNA. However, serious difficulties arise when manipulating very large DNA molecules. One set of the problems has given way to recent advances in the field of electrophoresis which utilize rotating gels or pulsing electric fields. Using these new techniques, it is now possible to fractionate by length DNA molecules as long as 10 megabases (Cantor, et al., 1988; Cantor and Schwartz, 1984; Serwer, 1987; U.S. patent application, Ser. No. 212521 incorporated herein by reference).

Not the least of the problems remaining for workers wishing to use the new techniques of rotating gel electrophoresis (RGE) and pulsed-field electrophoresis is the availability of stable, reproducible length standards which provide discrete markers of known length. The most useful primary length standards used in the past have been obtained by annealing single-stranded ends of mature, 49 kb bacteriophage λ to form concatemers (end-to-end multimers of the monomeric DNA).

However, λ standards suffer limitations due to their short terminal repeats (12 bp); damage to these ends either before or during the concatemerization process limits the length of the concatemers. The concatemers of λ phage that do form are not particularly stable to denaturation since the overlapping ends are quite short. Thus, when used under conditions that even mildly denature DNA, such as elevated temperature, bacteriophage λ standards are destabilized and rendered useless as DNA length markers.

Additional problems arise with the λ standards if the standard preparation is allowed to sit for even short periods of time. Since the concatemerization which occurs with the λ DNA is non-enzymatic, these preparations tend to further concatemerize over time giving rise to non-reproducible results from one usage to the next and to a much shorter shelflife. The only successful manner in which to prevent deterioration of λ standards is to maintain them in significantly diluted solutions which requires at least one subsequent concentration step or which renders them too dilute for many applications.

Other viruses with terminally repetitious, double-stranded DNA are the T-odd bacteriophages. During infection, T7-related bacteriophages produce linear, end-to-end concatemers of the unit length viral genome. These concatemers are then incorporated as a single viral genome into preformed coat-protein shells called proheads. Although the exact mechanism for construction and cleavage of the concatemers and the subsequent packaging of this DNA into the bacteriophage coat-protein has been the subject of extensive study, it is not yet completely understood.

The details of some of the physiological events for the T7 bacteriophage began to be known around 1970 when investigators noticed "intermediates" during the intracellular DNA synthesis of several species of bacteriophage (Kelly and Thomas, 1969). By the middle of the 1970's, workers using rate zonal centrifugation and electron microscopy established that the formation of DNA concatemers inside the bacterial host cell did not arise from normal bacteriophage recombination (Miller et al., 1976). Subsequently, it was found that most of this type of concatemer did not contain integral multiples of the monomeric length T7 DNA (Serwer, et al., 1987).

Using restriction endonuclease analysis, it was possible to determine that most of the concatemeric DNA from T7-infected cells consisted of bacteriophage genomes arranged in a linear head-to-tail fashion. (Langman et al., 1978; Serwer, et al., 1987). Adjacent genomes within a concatemer were found to overlap for a length of about 200 base pairs which was far greater than the overlapping 12 base pair tails of λ bacteriophage DNA (Langman et al., 1978). Later, the length of the T7 terminal repeat was found to be 160 base pairs (Dunn & Studier, 1983).

Advances in a similar double-stranded bacteriophage, T3, established that an in vitro system could be used in which mature DNA purified from T3 was packaged into the empty viral head precursors. The concatemers generated by this method were visualized by electron microscopy and by their incorporation into infectious bacteriophage particles (Fujisawa et al., 1980). The emphasis of subsequent research using the T3 bacteriophage has been to refine the in vitro system for the purposes of maximizing the T3 DNA packaging reaction when conducted with unconcatemerized, monomeric DNA (Hamada et al., 1986; Shibata et al., 1987).

Studies of organization and expression of T7 DNA led to the determination of its nucleotide sequence and the localization of some of the genetic elements responsible for the bacteriophage functions in the host cell (Studier and Dunn, 1983; Dunn and Studier, 1983; Lee and Sadowski, 1984; White and Richardson, 1987). It is important to note that all of the studies involving the use of mutants of T7 and of processing of bacteriophage DNAs have focused upon the complete maturation cycle. Though the concatemers formed by these systems were manipulated extensively and fractionated by centrifugation, nothing in the literature suggested that the concatemeric products of the T7 bacteriophage themselves could be viewed as an end-product useful as a DNA length standard for which a maximized system might be derived.

Attempts by one of the inventors of the current invention to fractionate in vivo T7 concatemeric DNA by agarose gel electrophoresis initially met with very limited success (Serwer and Greenhaw, 1981; Serwer, et al. 1987). Only a minority of these in vivo concatemers formed bands at integral ($\eta$) length the multiples of the T7 monomer; the longest of these had an O of 4. It was not feasible to control the natural viral metabolism in a manner to produce stable, discrete DNA length standards. It was necessary to overcome these problems in order for the T7 concatemers, which possessed several advantages to the concatemers of λ DNA, to be used as DNA length markers.

SUMMARY OF THE INVENTION

Accordingly, the present inventors have now discovered a successful method for enzymatically joining segments of DNA to form concatemers useful as DNA length standards. These concatemers, formed in vitro, are primarily found as discrete-length classes each representing an integer multiple of substrate DNA (Son, et al., 1988). During rotating gel electrophoresis, these discrete-length concatemers form a series of bands referred to as a ladder.

It is the intent of the invention, therefore, to provide the benefits of using these DNA concatemers by disclosing a method for the production of stable, reproducible standards via techniques that allow precise control of length distribution. The invention provides an unexpectedly successful method for producing concatemeric DNA molecules with a distribution of defined and discrete lengths. In a preferred embodiment, it achieves this by adding purified DNA to extracts of bacterial cells which have been infected with selected bacteriophage mutants, buffered in a unique manner to accommodate temperature fluctuations, and then controlling the ensuing concatemerization of DNA in the buffered cell extracts in a precise way using a surprising property of the packaging enzymes of the extract.

Therefore, according to the present invention there is provided a method for producing ranges of DNA length standards. It is, for instance, possible to achieve concatemerization of exonuclease-digested, exogenous DNA added to mere extracts of bacterial cells themselves. However, by infecting the cells with either nonmutated T7 or a related bacteriophage or with bacteriophage mutated in one or more important genes, significant improvements can be realized in production of concatemers.

For example, the inclusion of T7 gene product 6 increases concatemerization without relying on addition of exogenous exonuclease to the extract. Furthermore, by using extracts from bacterial cells infected with bacteriophage having mutations in one or more of the genes responsible for bacteriophage DNA synthesis, unwanted endogenous DNA synthesis by the infecting bacteriophage is virtually eliminated. Generally, in order to provide these gene products in the eventual extract, it is advantageous to produce two separate, complementing extracts each individually incapable of promoting bacteriophage DNA synthesis but, in combination, completely capable of doing so. By mixing the separately prepared extracts, one achieves an extract fully capable of concatemerization but which has no significant background of DNA prior to the addition of substrate DNA.

Additionally, it has been demonstrated that the substantial elimination of packaging in the extracts is an advantageous component of the present invention. This can be achieved by mutating one or more of the genes responsible for packaging T7 DNA. By doing so, it is possible to produce concatemers by incubating the extract with substrate DNA at 30° C., a temperature at which packaging would otherwise occur. However, the maximal production achieved by the present invention limits packaging and the rate of concatemerization by either lowering the temperature to 0°-4° C. or by a combination of low temperature and mutation of one or more packaging genes.

The resulting product of the process described herein is virtually a custom-made-to-order range of standards selected by altering the conditions of the reaction or by altering the substrates themselves in kind or concentration. By varying the mutant combinations, the extract reaction conditions or the substrate DNA, it is possible to produce a variety of standard preparations. For instance, by reducing the concentration of the substrate DNA used, progressively more open circular DNA is produced. In this manner, open circular DNA useful as a DNA standard in its own right can be produced for DNA as long as $4\eta$.

The preparations produced in accordance with the present invention provide a readily usable, highly concentrated and very stable source of DNA length standards. They can be applied in the determination of the lengths of unknown DNA fragments using a wide variety of typically encountered electrophoretic methods including the state-of-the-art rotating gel or pulsed-field techniques.

DETAILED DESCRIPTION OF THE PREFERRED EMBODIMENTS

Figure 1:
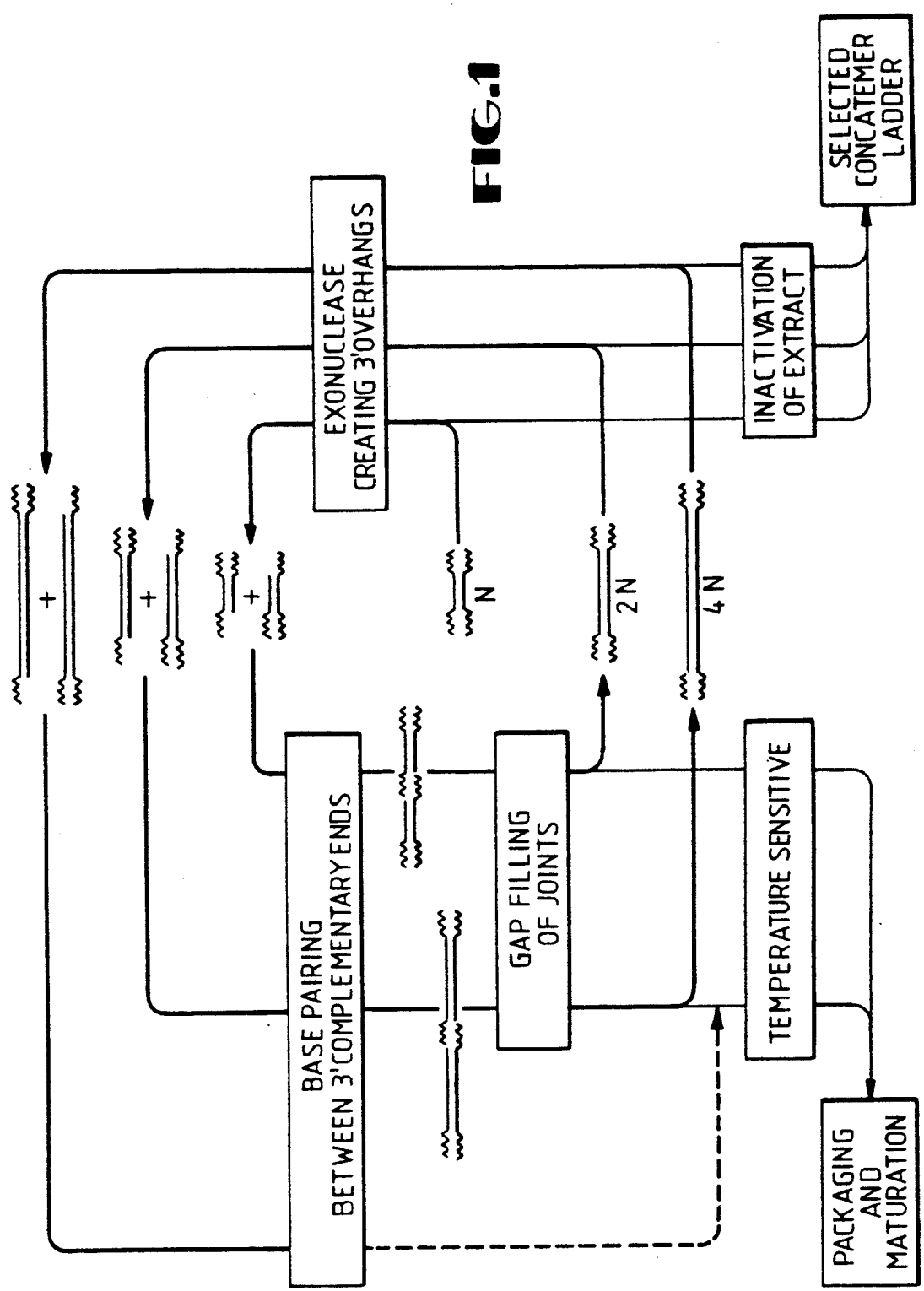
FIG. 1—Concatemerization cycle of the invention. Depicted here is the leading theory for the mechanism of concatemerization in T7 bacteriophage as it would occur in the extract produced by the method claimed.

Therefore, in accordance with the present invention, there is provided a method for the production of DNA length standards useful in sizing long DNA molecules. In a preferred embodiment, specific mutant combinations are used to produce the necessary bacteriophage gene products and to exclude unwanted DNA and, in some cases, bacteriophage gene products from the extract. While it is possible to use uninfected cells as described further herein, the significant advantage of using bacteriophage extracts allows formation of at least 10-11 higher multimers.

Certain gene products have been found to be advantageous when included in the concatemerization extracts. For instance, one may exploit the exonuclease activity of the bacteriophage gene 6 product either endogenous to the extract or added exogenously to provide the necessary 3' overhangs. Under the conditions existing in the normally infected cell, the 3' overhangs are believed to be produced through incomplete DNA synthesis toward the 5' end of the single-stranded template and not by the functioning of the gene 6 product. It is believed that several other exogenously added exonucleases can substitute in vitro for gene 6 product. Exonuclease III of E. coli, an enzyme that produces 5' overhangs, is an example successfully tried by the inventors.

The use of bacteriophage having amber mutations in certain genes (for example, Dunn and Studier, 1983) allows one to exclude unwanted bacteriophage gene products from the reaction mixtures. Mutations can be made in any of the genes required for bacteriophage DNA metabolism, including gene 3, 4 or 5 or combinations of these genes. Gene 4 and 5 mutations eliminate DNA synthesized in vivo from the extracts. Likewise, the use of mutations in bacteriophage genes required for packaging the concatemers into viral coat proteins can be made; these genes include 8, 9, 10, 18 or 19 or combinations of these genes.

Practice of the invention is facilitated by the surprising discovery that concatemerization and packaging can be uncoupled; concatemerization is slowed and packaging is virtually stopped by lowering the temperature to about 0°-4° C. Substrate-extract mixtures incubated for one hour at 0° C. produce about $1 \times 10^9$ fold fewer plaques than similar mixtures incubated at 30° C. Even when the reactions are allowed to proceed overnight, the ratio remains as high as $1 \times 10^4$ to $1 \times 10^5$. By exploiting the difference in sensitivity to temperature, one may virtually eliminate packaging of concatemers while simultaneously allowing successive cycles of concatemerization to proceed at a slowed and, therefore, more easily controlled rate. Finally, in order to take advantage of this distinction between the extract activities, the inventors had to design a buffering system which would provide adequate buffering capacity at both the higher and the lower temperatures utilized in the method.

The concatemers produced by the methods disclosed here may be used as discrete standard markers of exactly known lengths for gel electrophoresis. In its most preferred embodiment, precise ranges of the concatemeric standards can be produced in a made-to-specifications process since the methods provide a previously unattainable technique for the precise control of concatemerization. The products of these methods, aside from their uniquely controlled production, provide distinct advantages as DNA length standards over those currently available. The present method is highly reproducible and convenient given the proper techniques and starting materials. With the aid of the present disclosure, the production of the concatemers would be easily accomplished in the working laboratory by one of skill in the art.

A variety of alternatives exist which provide flexibility to the methods described. For example, under certain conditions, one may prefer to eliminate the infection of the host cell altogether. By doing so, the range of possible multimers is significantly reduced but the need and expense required to generate the infecting bacteriophage is eliminated. Alternatively, the skilled worker may choose to use a single infecting bacteriophage to supply the gene product 6. In another embodiment, an exonuclease from an exogenous source, for example, purified gene product 6 or E. coli exonuclease III, may be used to treat the substrate DNA to create the overhangs necessary for concatemerization. Such exonuclease-treated substrate DNA can be produced either by first treating the substrate DNA with the selected exogenous exonuclease and then mixing the substrate DNA with the bacterial cell extract, or alternatively, by simply preparing a mixture of the bacterial cell extract, the substrate DNA, and the exogenous exonuclease. Accordingly, the term "exonuclease-treated" DNA is expressly intended to refer to DNA treated in accordance with either of these procedures.

Finally, in a highly preferred embodiment, one may infect separate bacterial cell cultures with separate bacteriophage. These bacteriophage are selected from a collection of double amber mutants, each of which contains a mutation in a different bacteriophage gene required for DNA synthesis and also each of which contains a mutation in the same bacteriophage gene required for packaging the concatemers. In other words, one may separately infect at least two bacterial cell cultures each with a different T7 bacteriophage where; (1) the infecting bacteriophage are selected so that functional T7 gene 6 is present in either one of the bacteriophage or in the combination of both, and where (2) one bacterial cell culture is infected with a first T7 bacteriophage characterized further in that the first bacteriophage contains mutations in at least one of the T7 genes responsible for viral DNA synthesis and in at least one of the T7 genes responsible for packaging of the viral DNA, and where (3) the other bacterial cell culture is infected with a second T7 bacteriophage characterized further in that the second bacteriophage contains mutations in at least one of the T7 genes responsible for viral DNA synthesis distinct from that selected in the first bacteriophage and which contains mutations in the same T7 gene or genes responsible for packaging of the viral DNA as was mutated in the first bacteriophage.

For example, the first double mutant selected might be T7$_{4,9}$ where gene product 4 is required for DNA synthesis and gene product 9 is required for packaging. The second double amber mutant could be T7$_{5,9}$ where gene product 5 is required for DNA synthesis but is different from gene product 4 and where gene product 9 is again mutated as in the first double mutant eliminating it altogether from the mixed extract. Alternatively, it may be preferred to use bacteriophage having mutations in gene 19 instead of in gene 9.

In yet another embodiment, concatemerization is carried out on extracts devoid of functional gene product of T7 gene 3. With this embodiment, substrate DNA may be incubated with either extracts of bacterial cells infected with a single T7 bacteriophage having a mutation in gene 3 or with a mixture of extracts of separately infected bacterial cells, where each of the infecting bacteriophage has a mutation in gene 3.

The general method of the invention can be applied in its most preferred embodiment to strains of E. coli. Even more preferred are non-permissive E. coli host strains such as E. coli BB/1. Alternatively, similar enteric hosts for T7 can be utilized, namely certain strains of Shioella or Yersinia.

The selection of an optimal buffer in which to extract the host cells may markedly enhance the success of the method. Such a buffer should retain the lysis-enhancing characteristics of Tris buffers. Additionally, the buffer should have the capacity to function at temperatures below 30° C. In its most preferred embodiment, the extraction buffer should be composed of a Tris-phosphate buffer at about pH 7.4. Such a buffer combines the attributes of Tris with the temperature capacity of phosphate buffers.

The substrate DNA added exogenously to the concatemerization extract can be any one of a number of DNAs. It will typically be a T7-related bacteriophage DNA (such as T7 or T3) with the characteristic long terminal repeats of this group of bacteriophage. T5 DNA has been tried by the inventors but presents problems as yet unresolved. Alternatively, the substrate DNA may comprise at least some nonviral DNA, for example synthetic DNA. In yet another embodiment, the substrate DNA may be a mutant variety of the selected bacteriophage DNA. In its most preferred embodiment, however, the DNA will be that of non-mutant T7 bacteriophage.

One may run the concatemerization reactions at 30° C. or at a lower temperature, for example, about 0°–4° C. This may be done at the lower temperatures without using bacteriophage mutated in the packaging genes, but in another embodiment may be accomplished at either temperature range in combination with such mutant bacteriophage. In its most preferred embodiment, the method would utilize mutation in at least one of the packaging genes of the infecting bacteriophage in combination with a reaction temperature of about 0°–4° C.

Upon completion of the desired level of concatemerization, one may inactivate the enzymes of the extract by a variety of means including the use of anionic detergents. While the exact mechanism for concatemerization is still unknown for T7, it involves at least some required enzymatic activity. It is the intention of the invention to produce a stable concatemer mixture by inactivating the enzymatic concatemerization activity of the extracts with detergent. These detergents may include lauryl sulfate and N-lauroylsarcosine (sarkosyl). In addition, it will often prove advantageous to treat the concatemer product solution with a non-specific protease. These proteases may include subtilisin or protease K. The T7 concatemers thus produced have been stable for as long as 12 months or greater.

Finally, since large DNAs are quite susceptible to shearing forces, it is advantageous to minimize handling and the resulting shearing force it produces. Therefore, in a preferred embodiment one may trap the product concatemers in agarose blocks conveniently sized to allow ease of use in various electrophoretic procedures (Cantor and Schwartz, 1984).

The methods described above can be depicted as a cyclical concatemerization (FIG. 1). The concatemerization process begins at the center of the diagram with a monomeric (0) DNA substrate molecule and proceeds in a cyclical manner through three stages before advancing to the next turn of the cycle; (1) gene product 6 or an enzyme with similar characteristics (for example E. coli exonuclease III) creates single-stranded overhangs via an exonuclease activity on each of the existing ends of the substrate DNA, (2) two molecules of the exonuclease-digested substrate, each with a different chain digested, are joined by base pairing between the complementary overhangs to produce a duplex molecule, (3) limited DNA repair takes place over the joint between the pair of substrate molecules and some may be covalently joined by ligation producing a $2\eta$ substrate DNA for the next turn of the cycle.

Under normal conditions, both in the cell and in the extracts, concatemers formed in this manner undergo maturation back into the monomeric bacteriophage genome and are packaged into the coat-protein of the viral head. The invention teaches the exploitation of an unexpected differential temperature sensitivity between those reactions leading to packaging and maturation and those reactions which extend the concatemer lengths. Since the packaging reaction is eliminated, selection of specific time points at which the concatemerization reaction is inactivated gives rise to a given range of concatemers.

Though it is not shown in this diagram for the sake of simplicity, it can be seen that concatemers with odd-numbered multiplicities can arise by combinations of an $\eta$ sized fragment base pairing with a $2\eta$, $4\eta$, etc. sized fragment. Additionally, it can be seen that the head-to-tail hybridization between ends of the same molecule could produce circular molecules. Such molecules have been seen in the in vitro concatemers as open circles of DNA for multimers of up to $4\eta$.

Furthermore, it can be seen in FIG. 1 and as described further here that circular DNA molecules can readily be formed by the annealing of the complementary overhangs of a single monomer length molecule or of any of the higher multimers. It has been found by the inventors that by limiting the initial substrate DNA concentration one may generate proportionally more circular standards in comparison to linear molecules. The invention, therefore, encompasses production of circular standards as well as production of the preferred linear standards.

The following examples describe the actual steps necessary to generate a selected range of T7 concatemers and to visualize them after electrophoresis by RGE. These examples are intended to illustrate certain aspects of the present invention and should not be construed as limiting the claims thereof.

EXAMPLE I

The following protocols describe the particular experiments which led to the disclosed invention. These experiments were designed to study both the concatemerization and the packaging reactions. The results conclusively demonstrate that the in vitro reaction of crude extracts of infected cells can selectively concatemerize DNA while limiting packaging.

A. BACTERIOPHAGE AND HOST STRAINS

Bacteriophage T7 amber mutants in gene 4, 5, 9, or 19 were described by Studier (1969). A T7 amber mutant is indicated by T7 with the number of the mutated gene(s) in subscript. The double mutants, $T7_{4,9}$ and $T7_{5,19}$, were constructed with a genetic cross and tested by complementation. The permissive host for amber mutants was *Escherichia coli* 0-11'. The nonpermissive host and the host for wild-type T7 ($T7_{wt}$) was *E. coli* BB/1.

B. MEDIA, BUFFERS, AND REAGENTS

Bacteriophages were stored in Tris/Mg buffer (0.2 M NaCl, 0.01M Tris-Cl, pH 7.4, 0.001M $MgCl_2$) NET buffer was used for storing DNA (0.1M NaCl, 0.01M Tris-Cl, pH 7.4, 0.001M EDTA). Extract buffer was used for preparing in vitro assembly extracts (0.1M NaCl, 0.02M Tris-phosphate, pH 7.4, 0.006M $MgSO_4$, 10 μg/ml gelatin). Stop buffer was used to terminate in vitro assembly (0.1M NaCl, 0.1M EDTA, 0.033M Tris-Cl, pH 7.5, 1% Sarkosyl, 36 μg/ml RNase A). Sample buffer (for electrophoresis) was 55% sucrose, 400 μg/ml bromphenol blue, 0.01M sodium phosphate, pH 7.4, 0.001M EDTA. Electrophoresis buffer, used for RGE, was 0.01M sodium phosphate, pH 7.4, 0.001M EDTA. The protease, subtilisin, and its inhibitor, phenylmethylsulfonyl fluoride (PMSF), were purchased from Sigma Chemical Co.

Bacteria were grown in 2X LB medium: 20 g bacto tryptone, 10 g yeast extract, 5 g NaCl, 1000 ml water. Seakem LE agarose, obtained from the Marine Colloids Division of FMC Corp., was used to form all gels for electrophoresis. Restriction endonuclease XbaI was purchased from New England Biolabs (Beverly, Mass.).

C. MATURE BACTERIOPHAGE DNAs

To obtain mature T7 DNA, bacteriophage $T7_{wt}$ was grown in 2X LB medium and purified as previously described (Serwer, 1980). DNA was extracted from T7 with phenol as described in Maniatis, et al. (1982). The DNA was stored in NET buffer at 4° C. and used as a substrate for concatemerization within 6 months. The mature DNAs of bacteriophage T4 and T5 were obtained as described in Serwer (1980). These DNAs were used as markers for the length of linear, double-stranded DNA. The length of T7 DNA is known to be 39.936 kb (Dunn and Studier, 1983). The reported lengths of T5 and T4 DNAs vary but a reasonable consensus appears to be 111-116 kb for T5 (McCorquodale, 1975) and 170 kb for T4 (Kutter and Ruger, 1983). The fragments of HindIII digests of bacteriophage λ DNA were used to mark the positions of linear DNA shorter than mature T7 DNA. The HindIII fragments visible here had lengths of 22.1, 8.82, 6.12, and 4.03 kb (Wellauer et al., 1974). The restriction enzyme HindIII digest used was purchased from Bethesda Research Laboratories (Gaithersburg, Md.). Bacteriophage λ DNA, 48.50 kb long (Sanger et al., 1982), was purchased from the same source. To cyclize λ DNA, the procedure described in Serwer and Hayes (1987) was used.

D. PREPARATION OF INFECTED CELLS FOR IN VITRO CONCATEMER FORMATION

A culture of *E. coli* BB/1 was grown to $4 \times 10^8$/ml in 2X LB medium with aeration at 30° C., and was then infected with $T7_{4,9}$ (m.o.i.=5). At 19-20 minutes after infection, the cells were chilled to 0° C. and pelleted at 10,000 rpm for 10 minutes in a Beckman J-20 rotor. The pellet was washed once in extract buffer at 0° C. and then resuspended in extract buffer in a volume 1/350X that of the infected culture. The resuspended cells were frozen at −70° C. Frozen cells infected with $T7_{5,19}$ were also prepared by the procedure described above.

E. IN VITRO CONCATEMER FORMATION

To prepare an extract for in vitro concatemer formation, infected cells frozen as described above were thawed with vortexing at 4° C. after adding a 1/50 vol of 10 mg/ml lysozyme in 0.015M Tris-Cl, pH 8.0, 0.0075M $MgCl_2$, 0.01M EDTA. Subsequently, the lysates were incubated at 0° C. for 10 minutes and were clarified by centrifugation in an Eppendorf tabletop centrifuge at 4° C. for 2 minutes (15,000 rpm). After clarification, a portion of a $T7_{4,9}$ extract was added to an equal volume of a $T7_{5,19}$ extract. To this mixture was added a 0.25X vol of 50% dextran-10 in extract buffer. Two final additions were made: (a) a 0.111X volume of 0.1M $MgSO_4$, 0.02M ATP, 0.025M spermidine, pH 7.4, and (b) a 0.00025X volume of β-mercaptoethanol. This mixed extract will be referred to as $T7_{4,9}+T7_{5,19}$ extract. After the final additions, this mixture was held on ice for no more than 1 hour before addition of DNA and incubation, as described below. Extracts prepared as described above and analyzed by agarose gel electrophoresis-ethidium bromide staining (without addition of DNA), as described below, had no detectable background of DNA. However, if the clarification was omitted after thawing of infected cells, there was a detectable background of monomeric DNA. This DNA presumably was released from infecting bacteriophage that had absorbed to, but had not injected their DNA into bacteria.

F. INACTIVATION OF IN VITRO REACTIONS AND ANALYSIS OF DNA BY RGE

Reactions in the extract-substrate DNA mixture were inactivated to prepare the samples for analysis by rotating gel electrophoresis using the following procedure. A 10X volume of stop buffer was added to the mixture and it was incubated at room temperature for 30 minutes, followed by an additional incubation at 75° C. for 10 minutes (second incubation is optional). The latter incubation, but not the former, would completely release from its capsid any of the DNA packaged in mature T7. Subsequently, a 0.043X volume of 30 mg/ml subtilisin was added, followed by incubation at 30° C. for 1 hour and at 4° C. overnight. Omission of the subtilisin resulted in DNA that arrested near the origin of electrophoresis, presumably because of aggregation with proteins. The digestion with subtilisin was stopped by adding 1 μl of 0.01M PMSF to 40 μl of digested sample.

Next, 5 μl of sample buffer was added and the entire amount was layered in the sample well of a gel for RGE. To avoid degradation by shear (Davison, 1959), the DNA was pipetted slowly with a pipet that had an inner diameter of 1 mm. The gel used for RGE was a 1.5% agarose gel, poured in electrophoresis buffer as previously described (Serwer, 1987) and submerged beneath electrophoresis buffer. After layering DNA in sample wells, the DNA was electrophoretically driven into the gel for 10 min at 3 V/cm, without rotation of the gel. Reciprocal, periodic rotation of the gel to two positions was then started and electrophoresis was continued at the indicated voltage gradient and temperature, as previously described (Serwer, 1987). The angle between the two positions ($\Psi$ in Serwer, 1987) was 144°. The time between rotations (i.e., the time that the gel was stationary) was 20 seconds and the speed of rotation was 100°/second. Temperature was controlled to within ±2% by circulating buffer through a temperature-controlled water bath.

After electrophoresis, the gel was stained for 2-3 hours in 1 μg/ml ethidium bromide dissolved in electrophoresis buffer. Gels were photographed on Kodak Tri-X film through a Tiffen 23A (orange) filter during illumination with a 300-nm (peak wavelength) ultraviolet transilluminator.

G. CONCATEMERIZATION AT 0° C.

Figure 2:
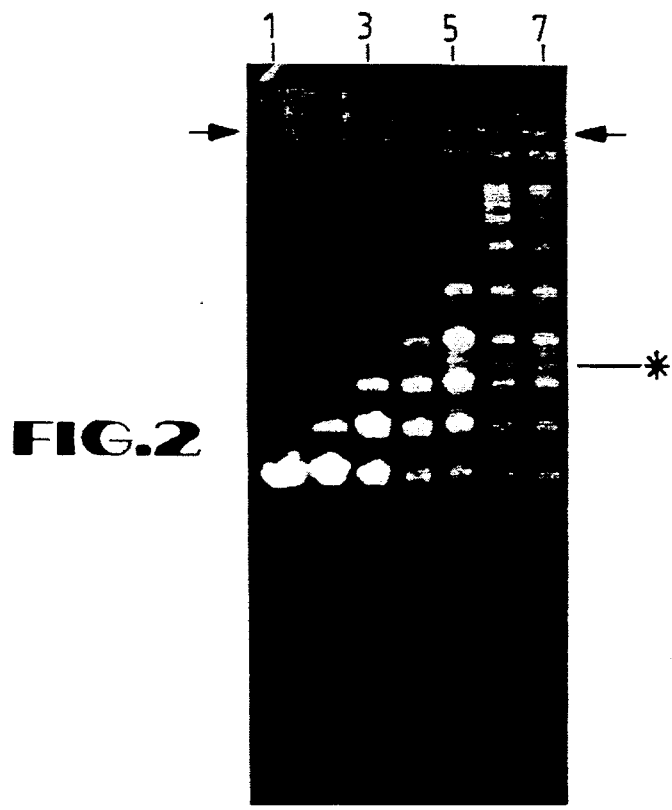
FIG. 2—Formation of concatemers at 0° C. The experiment of FIG. 2a was performed at 0° C. The times (minutes) of quenching used were (1) 0, (2) 3, (3) 6, (4) 9, (5) 12, (6) 15, (7) 18. The arrow indicates the direction of electrophoresis, the arrowheads indicate the origin of electrophoresis, and the asterisk indicates a band of circular DNA deduced from data not included herein.

The following experiment describes results obtained when extracts prepared as described above were incubated and used to selectively inhibit packaging almost completely while allowing progressive concatemerization of substrate DNA to proceed at a controlled rate. The methods used were identical to those above except that incubation was carried out at about 0°-4° C. as opposed to 30° C. After 3 minutes at 0° C., the first band of concatemer had formed (FIG. 2, lane 2; a 0-minute sample was analyzed in lane 1). As the time increased to 6, 9, 12, 15, and 18 minutes, bands of larger concatemers progressively formed (FIG. 2, lanes 3-7, respectively). In comparison with results obtained at 30° C., FIG. 3, (a) the intensity of bands was increased at the expense of the continuous background of DNA, and (b) concatemerization was slowed. There was no detectable packaging of DNA in FIG. 2. In a separate experiment, the titer of infectivity produced after overnight incubation at 4° C. was $8.5 \times 10^7$, significantly above background, but 3-4 orders of magnitude below a titer of $1.8 \times 10^{11}$ achieved at 30° C. after a 60-minute incubation with the same extract. Thus, incubation at 0°-4° C. inhibits packaging significantly more than it inhibits concatemerization.

These results demonstrate the significant advantage afforded by the use of lower temperatures for the formation of distinct concatemer bands. This is particularly evident when comparison is made with the equivalent reactions at 30° C. described in FIG. 3.

H. CONCATEMERIZATION AT 30° C.

For sake of comparison, experiments were carried out at both higher (30° C.) and lower (0°-4° C.) temperature ranges. To observe the conversion products of mature T7 DNA as a function of time at 30° C. in a $T7_{4,9} + T7_{5,19}$ extract, the conversion products were observed by RGE at 2.5, 5, 10, 15, 20, 30, 45, and 60 minutes after the start of incubation. By 2.5 minutes, almost all DNA migrated more slowly than monomeric T7 DNA (FIG. 3a, lane 1). Both a continuous background of DNA and DNA that formed bands was observed. As shown below, all but a small fraction of this DNA is linear. The profile did not change at 5 minutes (FIG. 3a, lane 2), and was also not altered by preincubation of the DNA-lysate mixture at 0° C. for 30 minutes (FIG. 3b, lane 1), a procedure that caused extensive concatemerization. By 10 minutes an increase in the amount of monomeric DNA was observed (FIGS. 3a and 3b, lanes 3). This increase in monomeric DNA continued at 15-60 minutes (FIG. 3a, lanes 4-8) and its kinetics were not altered by the preincubation (FIG. 3b, lanes 4-8). To determine whether or not the monomeric DNA present at 60 minutes was packaged, before quenching a duplicate 60-minute sample was digested with DNase I. The result was digestion of all concatemeric, but not most monomeric, DNA (FIG. 3b, lane 9). Thus, most of the monomeric DNA at 60 minutes was packaged. The absence of an effect of preincubation on the rate of packaging suggests that concatemerization is not rate limiting for DNA packaging.

As DNA was packaged in FIGS. 3a and 3b, the bands formed by concatemeric DNA became significantly more intense in relation to the continuous background and the average distance from the origin increased (and, therefore, the average length of a DNA molecule decreased). Both of these observations suggest that the DNA packaged was cut from concatemers. The six bands closest to the band of monomeric DNA were separated by a roughly constant nearest neighbor distance.

I. THE LENGTHS OF CONCATEMERS

Figure 3:
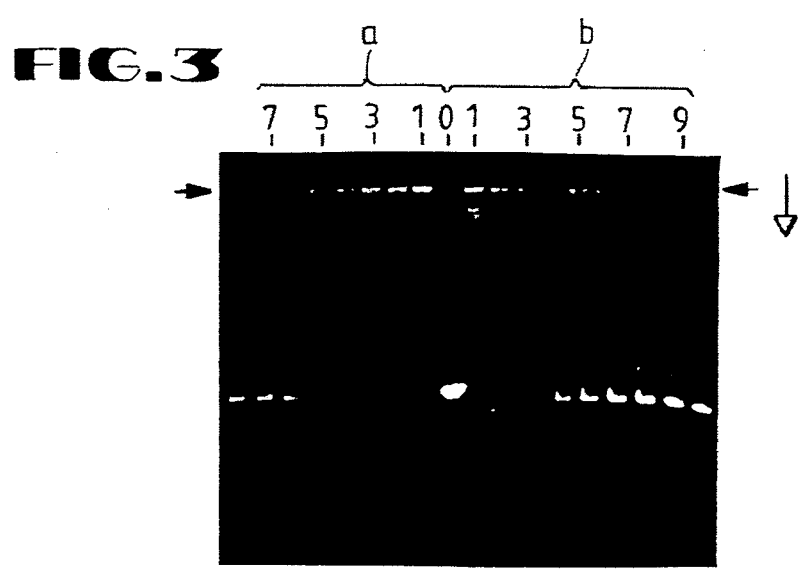
FIG. 3—Formation and packaging of concatemers in vitro. (a) A $T7_{4,9}+T7_{5,19}$ extract. Immediately after adding DNA, these mixtures were incubated at 30° C. for the times indicated below before quenching and analysis by RGE. (b) A second experiment was simultaneously performed, as described above, but with one alteration; the extract-DNA mixture was incubated at 0° C. for 30 minutes before incubation at 30° C. The following were the times (minutes) of incubation at 30° C. (number of lanes indicated): (0) 0, (1) 2.5, (2) 5, (3) 10, (4) 15, (5) 20, (6) 30, (7) 45, (8) 60, (9) 60 but with digestion by DNase I before quenching. The arrow indicates the direction of electrophoresis; the arrowheads indicate the origins of electrophoresis.
Figure 4:
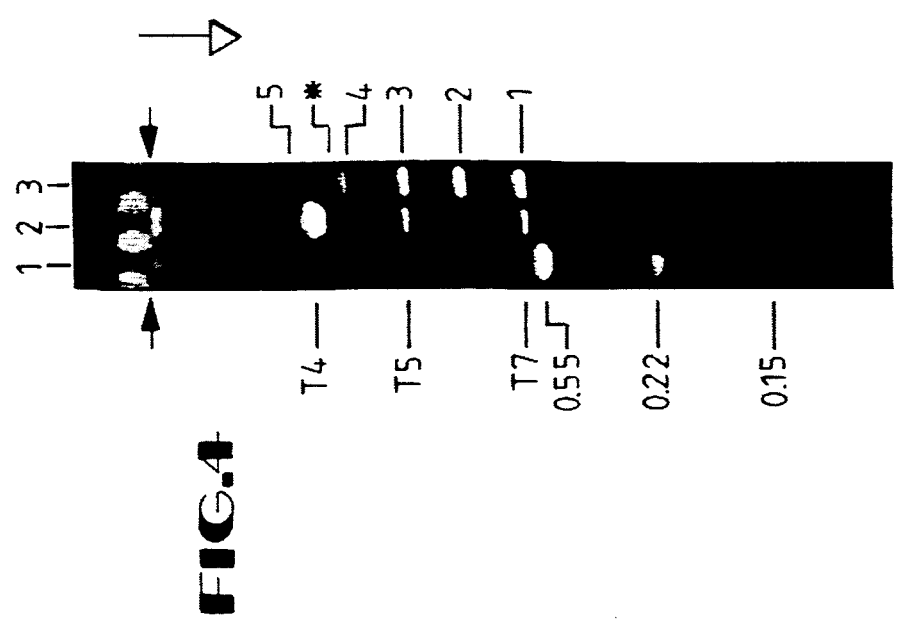
FIG. 4—Identification of bands. Subjected to RGE in the same gel were the following linear DNA length markers: lane 2, a mixture of the mature DNAs of bacteriophage T4, T5, and T7; lane 1, a restriction endonuclease HindIII digest of bacteriophage λ DNA. Lane 3 contained concatemers formed by a $T7_{4,9}+T7_{5,19}$ extract after 4 minutes at 0° C. The direction of electrophoresis is indicated by the arrow, the arrowheads indicate the origin of electrophoresis, and the asterisk indicates a band of circular DNA deduced from data not included herein. The positions of the fragments of the HindIII digest are indicated by their fraction of the length of mature T7 DNA.

To determine the lengths of the concatemers that formed bands in FIGS. 2 and 3, the positions of these bands in relation to the positions of bands formed by T4 and T5 DNA markers of known length were determined (FIG. 4). To increase the resolution of this analysis in the region covered by the markers (2-5X the length of monomeric T7 DNA), the voltage gradient was lowered to 2 V/cm. An additional consequence of this change in voltage gradient was some loss of resolution for longer concatemers. The position of the band of concatemer indicated by 3 at the right in FIG. 4, lane 3, is coincident with the position of the band formed by T5 DNA (lane 2). Because the length of T5 DNA has been found to be 0.93-0.97 times the length expected of a trimeric T7 concatemer, the DNA that forms band 3 is assumed to be a trimeric concatemer. The DNA that forms band 2 is assumed to be a dimeric concatemer. If so, then the data of FIG. 4 suggest that T5 DNA is 118 kb long, 3-7% longer than previously reported. Band 4 in lane 3, FIG. 4 is in the position relative to T4 DNA (lane 2) of a tetrameric concatemer. These data suggest that the bands in the constant spacing series observed in FIGS. 2 and 3 are formed by linear T7 concatemers that consist of n monomeric DNAs; $\eta$ is the band's number as indicated in FIG. 4. The largest value of 0 thus far observed is 15 (See FIG. 5). There was no obvious selection either for or against any concatemer in the experiments of FIGS. 2, 3 or 4.

EXAMPLE II

The methods of Example I were used here with the exception that both a pooled extract and an extract resulting from a single, mutant bacteriophage was compared. Concatemers were obtained either by using extracts of cells injected with $T7_{3,19}$ or a mixed extract produced by mixing an extract of cells infected with $T7_{4,9}$ with an extract of cells infected with $T7_{5,19}$ Extracts, either pooled $T7_{4,9} + T7_{5,19}$ or single $T7_{3,19}$, were divided into 10 μl aliquots. To each of these aliquots, mature T7 DNA was added to a final DNA concentration of 100 µg/ml. The aliquots were incubated either at 0°-4° C. (Lanes 1A-8A pooled extracts or lanes 1B-6B single extract) or at 30° C. (Lanes 9A-12A pooled extracts or 7B-11B single-extract).

Figure 5:
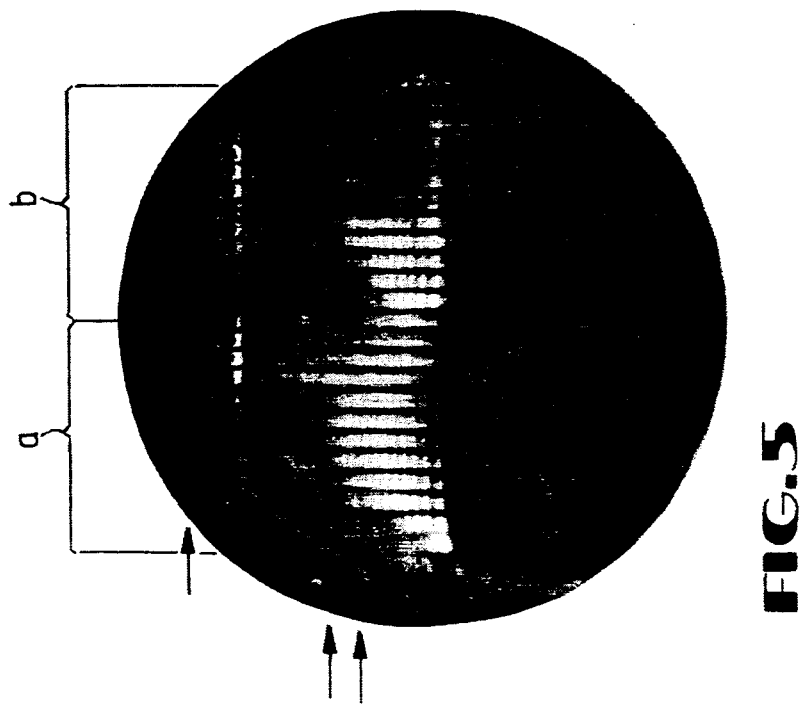
FIG. 5—Ladders formed by either a mixture of two double mutants or one double mutant. Extracts were divided into 10 μl aliquots. Either pooled extracts (A) of T7$_{5,19}$+T7$_{4,9}$ or single extracts (B) of T7$_{3,19}$ were used. To each aliquot T7 DNA was added to bring the final DNA concentration to 100 μg/ml and these aliquots were incubated at 0°-4° C. (Lanes A1-A8 and lanes B1-B6) or at 30° C. (Lanes A9-A12 and lanes B7-B11). Lanes to the extreme right and left contain mature T4, T5 and T7 as markers. Incubation times (minutes) were as follows; A1=3, A2=6, A3=9, A4=12, A5=15, A6=18, A7=21, A8=30, A9=2, A10=5, A11=7, A12=9; B1=10, B2=20, B3=30, B4=44, B5=56, B6=85, B7=2, B8=4, B9=6, B10=8, B11=11.

The extracts were incubated at the two temperature ranges for various time periods (See FIG. 5 legend) and the resulting concatemers were electrophoresed using RGE as described in Example 1. As can be seen in FIG. 5, concatemers were formed in both the pooled and single extracts. As incubation time increased, higher ranges of multimers were seen. The level of concatemerization of the single extract is comparable to that of the pooled extract. Additionally, as can be seen most clearly in lane A3, circular forms of the T7 DNA representing monomer (lower) and dimer (upper) are formed using the conditions described above.

EXAMPLE III

As stated above, in an alternative embodiment of the invention, substrate DNA may be treated with an exogenous exonuclease (for example, the exonuclease encoded by gene 6 of T7) by adding the exogenous exonuclease to the extract of infected or uninfected bacterial cells together with the substrate DNA, or by preincubating substrate DNA with the exonuclease and then adding the pretreated DNA to the extract. The following example describes these particular aspects of the invention.

Extracts are prepared essentially as described in the preceding examples except that infection of bacterial cells with selected bacteriophage is optional and substrate DNA (T7 DNA, in this example) is treated with exogenous exonuclease (T7 gene 6 exonuclease) according to either of the general procedures described below.

In the first case 1 microliter of T7 DNA at a concentration of 100 µg/ml in NET buffer together with 3-10 units of protein 6 (United States Biochemical Corporation) in 1 µl of (Protein-6)-assay buffer (50 mM Tris-HCl pH 8.1, 5 mM $MgCl_2$, 20 mM KCl, 5 mM 2-mercaptoethanol, 10 µg/ml of bovine serum albumin (Pentex —brand, Miles Laboratories) is added to 10 µl of an extract, which is then incubated at 0°-4° C. for 20 minutes, after which stop buffer is added. In the second case, 1 µl of T7 DNA (100 µg/ml in NET-buffer) is preincubated at +37° C. for 5 minutes with 0.3-1 units of protein 6 in 3 µl of (Protein-6)-assay buffer. The preincubation can be terminated by a heat treatment (by inactivation of protein 6 via heat treatment): the solution is made 0.1M with NaCl, incubated at +75° C. for 10 minutes, cooled slowly, and added to 10 microliters of extract at 0°-4° C. which is then incubated at 0°-4° C. for 20 minutes. The concatemers produced by these procedures may be further processed for electrophoresis as described in Example I.

Therefore, with a collection of concatemers such as described here, one could readily size linear DNA of unknown length in a manner similar to that used by the present inventors to determine the correct length. Since the concentration and stability of these standards remains high, one may conveniently store preparations at refrigerator temperatures until they are required.

More specifically, using appropriately gentle handling techniques, agarose gels or gel matrices of similar pore size can be loaded with the T7 concatemeric standards into wells adjacent to those loaded with unknown linear DNA samples. Upon electrophoresis the concatemeric standard will be resolved into a series of discrete bands (or ladder), where each band contains either monomeric substrate or a multimer thereof. The distance of migration of the unknown sample may then be compared to the distance migrated by the bands of the concatemeric standard to allow one to determine the size of the unknown sample. Rough estimates of size, useful in some situations, may be made by simply visualizing the positions of the band of unknown DNA relative to the position of the known standards. More exact determinations can be made by calculations and methods available to those of skill in the art, for example, by using a plot of length versus distance migrated.

The foregoing description of the invention has been directed to a particular preferred embodiment in accordance with the requirements of the patent statutes and for purposes of explanation and illustration. It will be apparent, however, to those skilled in the art that many modifications and changes in the methods and in the ultimate use of the product in a variety of applications may be made without departing from the scope and spirit of the invention.

For example, though the use of the product in gel electrophoresis is amply indicated herein, equivalent use can be made in any setting where size markers may be required. This may include scanning electron microscopy and gradient centrifugation techniques.

It will be further apparent that the invention may also be utilized with suitable modifications within the state of the art; for example, in combination with other DNA length standards such as λ and yeast chromosomes. It is the Applicant's intention in the following claims to cover all such equivalent modifications and variations which fall within the true spirit and scope of the invention.

REFERENCES

The following references may be useful in assisting understanding or practice of certain aspects of the present invention. Accordingly, each is expressly incorporated herein by reference.

1. Cantor, C. R. and Schwartz, D. C. 1984. U.S. Pat. No. 4,473,452, filed Nov. 18, 1982.
2. Cantor, C. R., et al. 1988. *Ann Rev. Biophys. Biophys. Chem.* 17:287-304.
3. Davison, P. F. 1959. *Proc. Natl. Acad. Sci. USA* 45:1560-1568.
4. Dunn, J. J. and Studier, F. W. 1983. *J. Mol. Biol.* 166:477-535.
5. Fujisawa, H., et al. 1980. Virol. 101:327-334.
6. Hamada, K., et al. 1986. Virol. 151:119-123.
7. Kelly, T. J. and Thomas, C. A. 1969. *J. Mol. Biol.* 44:459-475.
8. Kutter, E. and Ruger, W. 1983. In "Bacteriophage T7" (C. K. Mathews, E. M. Kutter, G. Mosig, and P. B. Berget, Eds.), pp. 219-245. American Society for Microbiology, Washington, D.C.
9. Langman, L., et al. 1978. *Can. J. Biochem.* 56:508-516.
10. Lee, D. D. and Sadowski, P. D. 1985. *Can. J. Biochem. Cell Biol.* 63:237-242.
11. Maniatis, T., Fritsch, E. F., and Sambrook, J. 1982. "Molecular Cloning: A Laboratory Manual," Cold Spring Harbor Laboratory, Cold Spring Harbor, N.Y.
12. McCorquodale, D. J. 1975. *Rev. Microbiol.* 4:101-159.
13. Miller, R. C., et al. 1976. *J. Mol. Biol.* 101:223-234.
14. Sanger, F., et al. 1982. *Mol. Biol.* 162:729-773.
15. Serwer, P. 1980. *Biochemistry* 19:3001-3004.

16. Serwer, P. and Greenhaw, G. A. 1981. In, *Electrophoresis '81* (Eds. Allen and Arnaud), pp. 627-633. Walter de Gruyter & Co., Berlin, FRG.
17. Serwer, P. 1987. *Electrophoresis* 8:301-304.
18. Serwer, P., et al. 1987. *J. Virol.* 61:3499-3509.
19. Serwer, P., and Hayes, S. J. 1987. *Electrophoresis* 224-246.
20. Serwer, P. 1987. U.S. patent application Ser. No. 212 521, filed Jun. 28, 1988, now U.S. Pat. No. 5,041,203.
21. Shibata, H., et al. 1987. *J. Mol. Biol.* 196:845-851.
22. Son, M., et al. 1988. Virol. 162:38-46.
23. Studier, F. W. 1969. *Virol* 39:562-574.
24. Studier, F. W. and Dunn, J. J. 1983. *Cold Spring Harbor Symp. Quant. Biol.* 47:999-1007.
25. Wellauer, P. K., et al. 1974. *Proc. Natl. Acad. Sci. USA* 71:2823-2827.
26. White, J. H. and Richardson, C. C. 1987. *J. Biol. Chem.* 262:8845-8850.
27. White, J. H. and Richardson, C. C. 1987. *J. Biol. Chem.* 262:8851-8860.

What is claimed is:

1. A method for sizing nucleic acid polymers of unknown length comprising the steps of:
    a) loading into one well of a gel matrix a quantity of a concatemeric DNA standard prepared by
        i) separately infecting at least two T7 infectable bacterial cell cultures each with a different T7 bacteriophage where the infecting bacteriophage is selected so that functional T7 gene 6 is present in at least one of the bacteriophage;
        ii) allowing the cells to synthesize bacteriophage proteins;
        iii) preparing extracts of the separately infected cells by lysing them in a buffered solution;
        iv) mixing the extracts;
        v) adding substrate DNA to the mixture and allowing enzymatic concatemerization of the substrate DNA to proceed for a selected time while limiting the packaging of the concatemeric DNA into bacteriophage head assemblies;
        vi) stopping enzymatic concatemerization by inactivating the enzymes of the extract which mediate concatemerization of the DNA concatemers; and,
        vii) treating the concatemers with a protease to enable their use as a concatemeric DNA size standard;
    b) loading into a separate well of the same gel matrix a quantity of a selected nucleic acid polymer;
    c) electrophoresing the standard and the selected nucleic acid polymer through the gel matrix under conditions and for a time sufficient to resolve the concatemeric standard into a series of discrete bands where each band contains either monomeric substrate DNA or concatemers thereof; and,
    d) determining the size of the nucleic acid polymer by detecting its position in the gel after electrophoresis relative to the position of at least one of the bands of the concatemeric standard.

2. A method for sizing nucleic acid polymers of unknown length comprising the steps of:
    a) loading into one well of a gel matrix a quantity of a concatemeric DNA standard prepared by
        i) separately infecting at least two T7 infectable bacterial cell cultures each with a different T7 bacteriophage where (1) the infecting bacteriophage are selected so that functional T7 gene 6 is present in at least one of the bacteriophage, and where (2) one bacterial cell culture is infected with a first T7 bacteriophage characterized further in that the first bacteriophage contains mutations in at least one of the T7 genes responsible for viral DNA synthesis and in at least one of the T7 genes responsible for packaging of the viral DNA, and where (3) the other bacterial cell culture is infected with a second T7 bacteriophage characterized further in that the second bacteriophage contains a mutation in at least one of the T7 genes responsible for viral DNA synthesis distinct from that selected in the first bacteriophage and contains a mutation in the same T7 gene or genes responsible for packaging of the viral DNA as was mutated in the first bacteriophage;
        ii) preparing extracts of the separately infected cells by lysing in a buffered solution where the buffer has a pH of about 7.4 and has the capacity to function below 30° C.;
        iii) mixing the extracts;
        iv) adding substrate DNA to the mixture and allowing enzymatic concatemerization of the substrate DNA to proceed for a selected time while further limiting the packaging of the concatemeric DNA into bacteriophage head assemblies by carrying out the concatemerization at a temperature maintained at about 0°-4° C.;
        v) stopping enzymatic concatemerization by inactivating the enzymes of the extract which mediate concatemerization of the DNA concatemers; and,
        vi) treating the concatemers with a protease to enable their use as a concatemeric DNA size standard; and
    b) loading into a separate well of the same gel matrix a quantity of a selected nucleic acid polymer;
    c) electrophoresing the standard and the selected nucleic acid polymer through the gel matrix under conditions and for a time sufficient to resolve the concatemeric standard into a series of discrete bands where each band contains either monomeric substrate DNA or concatemers thereof; and,
    d) determining the size of the nucleic acid polymer by detecting its position in the gel after electrophoresis relative to the position of at least one of the bands of the concatemeric standard.

3. The method of claim 1 where the first bacterial cell culture is infected with T7 bacteriophage having mutations in genes 4 and 9 and the second bacterial cell culture is infected with a T7 bacteriophage having mutations in genes 5 and 19.

4. The method of claim 1 where the packaging of concatemeric DNA is limited by carrying out concatemerization at a temperature that is sufficiently low to eliminate packaging but high enough to allow concatemerization.

5. The method of claim 4 where the temperature is maintained between about 0°-4° C.

6. The method of claim 1 where the packaging of concatemeric DNA is limited by using two bacteriophage infected cell extracts devoid of viral gene products selected from the group consisting of 8, 9, 10, 18, 19 and some combination thereof such that the mixed cell extracts lack completely one or more of the gene products responsible for packaging.

7. The method of claim 6 where the packaging of concatemeric DNA is further limited by carrying out the concatemerization at a temperature that is sufficiently low to eliminate packaging but high enough to allow concatemerization.

8. The method of claim 2 where the gene responsible for DNA synthesis in the first bacteriophage is selected from the group consisting of genes 4 and 5 and the gene responsible for packaging in the first bacteriophage is selected from the group consisting of genes 8, 9, 10, 18 and 19.

9. The method of claim 2 where the gene responsible for DNA synthesis in the second bacteriophage is different from that selected in the first bacteriophage and is selected from the group consisting of genes 4 and 5 and the gene responsible for packaging in the second bacteriophage is identical to that selected in the first bacteriophage and is selected from the group consisting of gene 8, 9, 10, 18 and 19.

10. The method of claim 1 or claim 2 where electrophoresis is accomplished by rotating the gel periodically and discontinuously in the presence of an electric field.

11. The method of claim 1 or claim 2 where the electrophoresis is accomplished using pulsed field gel electrophoresis.

12. The method of claim 1 or claim 2 where the buffered solution comprises a buffer of about pH 7.4 having the capacity to function at temperatures below 30° C.

13. The method of claim 1 or claim 2 where the substrate DNA is obtained from T7 bacteriophage or a mutant thereof.

14. The method of claim 1 or claim 2 where the substrate DNA is obtained from a T7-related bacteriophage or a mutant thereof.

15. The method of claim 1 or claim 2 where the substrate DNA contains nonviral DNA.

16. The method of claim 1 or claim 2 where the substrate DNA contains synthetic DNA.

17. The method of claim 1 or claim 2 where inactivation of the enzymes of the extract is accomplished by addition of a buffer comprising 0.1M NaCl, 0.1M EDTA, 0.033M Tris-Hcl, pH 7.5, 1% Sarkosyl and 36 ug/ml RNase A.

18. The method of claim 1 or claim 2 where the protease is subtilisin.

19. The method of claim 1 or claim 2 further comprising embedding the concatemeric DNA in an agar block.

20. The method of claim 1 or claim 2 where all T7 bacteriophage used for infecting the bacterial cells are incapable of producing a functional product of T7 gene 3.

* * * * *

UNITED STATES PATENT AND TRADEMARK OFFICE
CERTIFICATE OF CORRECTION

PATENT NO. : 5,294,545
DATED : March 15, 1994
INVENTOR(S) : Son et al.

It is certified that error appears in the above-indentified patent and that said Letters Patent is hereby corrected as shown below:

In Col. 3, ln. 1, replace "0" with --$\eta$--.

In Col. 7, ln. 26, replace the word "Shioella" with --Shigella--.

In Col. 8, ln. 17, replace "(0)" with --($\eta$)--.

Signed and Sealed this

Twenty-seventh Day of September, 1994

Attest:

BRUCE LEHMAN

*Attesting Officer*  *Commissioner of Patents and Trademarks*